US006432671B1

(12) United States Patent
Flohé et al.

(10) Patent No.: US 6,432,671 B1
(45) Date of Patent: Aug. 13, 2002

(54) TRYPAREDOXIN, EXPRESSION PLASMID, PROCESS OF PRODUCTION, METHOD OF USE, TEST KIT, AND PHARMACEUTICAL COMPOSITION

(76) Inventors: Leopold Flohé, Mascheroder Weg 1, Braunschweig D-38124 (DE); Everson Nogoceke, 500 E. 63rd St., New York, NY (US) 10021; Henryk Kalisz; Marisa Montemartini, both of Mascheroder Weg 1, Braunschweig D-38124 (DE)

( * ) Notice: Subject to any disclaimer, the term of this patent is extended or adjusted under 35 U.S.C. 154(b) by 0 days.

(21) Appl. No.: 09/330,914

(22) Filed: Jun. 11, 1999

Related U.S. Application Data

(63) Continuation of application No. PCT/EP97/06983, filed on Dec. 12, 1997.

(30) Foreign Application Priority Data

Dec. 12, 1996 (EP) .............................................. 96120015

(51) Int. Cl.⁷ ........................... C12P 21/06; C12Q 1/68; G01N 33/53; A61K 48/00; A61K 39/00

(52) U.S. Cl. ........................ 435/69.1; 435/6; 435/7.22; 435/24.3; 435/24.32; 435/320.1; 435/252.3; 435/255.3; 536/23.2; 536/24.3; 536/24.32; 424/93.1; 424/93.2; 424/93.21; 424/184.1; 424/265.1; 424/269.1

(58) Field of Search ............................ 435/76.22, 69.1, 435/342, 388.6, 975, 810, 189, 24.3, 320.1, 252.3, 258.3; 536/23.2, 24.3, 24.32; 424/93.1, 93.2, 93.21, 184.1, 265.1, 269.1

(56) References Cited

PUBLICATIONS

Carnieri et al 1993 (Mol Biochem.parasitol 61: 79–86).*
"Trypanothione Dependent Peroxide Metabolism in *Crithidia Fasciculata* and *Trypanosoma Brucei*", Henderson et al., XP–002057592, Molecular and Biochemical Parasitology 24, pp. 39–45, 1987.
"cDNA Expressed Sequence Tags of *Trypanosoma Brucei Rhodesiense* Provide New Insights Into the Biology of the Parasite", El–Sayed et al., XP–002057591, Molecular and Biochemical Parasitology 73, pp. 75–90, 1995.
"A Unique Cascade of Oxidoreductases Catalyses Trypanothione–Mediated Peroxide Metabolism in *Crithidia Fasciculata*", Nogoceke et al., XP–002057593, Bio. Chem. vol. 378, pp. 827–836, Aug. 1997.
"Trypanothione–Mediated Peroxide Metabolism in *Crithidia Fasciculata*", Kalisz et al., XP–002076002, Nov. 11, 1997 Abstract. XIII Geeting of Brazilian Society of Protozoology vol. 92, No. 1 Suppl.
"Sequence Analysis of the Tryparedoxin Peroxidase Gene From *Crithidia Fasciculata* and its Functional Expression in *Escherichia coli*", Monemartini et al., The Journal of Biological Chemistry, vol. 273, No. 9, pp. 4864–4871, Feb. 27, 1998.
International Search Report from PCT/EP97/06983 dated Sep. 18, 1998.

* cited by examiner

*Primary Examiner*—Mark Navarro
*Assistant Examiner*—Padmavathi Baskar
(74) *Attorney, Agent, or Firm*—Marshall, Gerstein & Borun.

(57) ABSTRACT

The present invention provides novel enzymes, tryparedoxins, their isolation from *Crithidia fasciculata*, a method for the production thereof in genetically transformed bacteria, and their use as molecular targets for the discovery of trypanocidal drugs.

9 Claims, 12 Drawing Sheets

```
     G   K   V   L   F   F   Y   F   S   A   S   W   C   P   P   15
  1  GGS AAR CTR GTS TTC TTC TAC TTC TCC GCG AGC TGG TGC CCG CCG

C   R   G   F   T   P   Q   L   I   E   F   Y   D   K   F   30
 46  TGC CGC GGC TTC ACG CCG CAG CTG ATC GAG TTC TAC GAC AAG TTC

H   E   S   K   N   F   E   V   V   F   C   S   W   D   E   45
 91  CAC GAG TCG AAG AAC TTC GAG GTT GTG TTC TGC TCG TGG GAC GAG

E   E   D   G   F   R   G   Y   F   A   K   M   P   W   L   60
136  GAG GAG GAC GGC TTT CGC GGC TAC TTC GCG AAG ATG CCG TGG CTT

A   V   P   F   A   Q   S   E   A   V   Q   K   L   S   K   75
181  GCG GTG CCG TTT GCG CAG AGC GAG GCG GTG CAG AAG CTG TCG AAS

H   F   N   V   E                                           80
226  CAS TTC AAC GTC GAG
```

Figure 2

```
-196                     gaagtatcttgtagtggtacacttctcacatacaaca
-159 caacttattctttgcttttcactttgtctgtgtgttgaagcactcgcacatc
-106 acgcctcgttgccgcaccgcgcacaaggctctacggtttcgctcacgctgagt
 -53 cggggtgcatgtatcacacccttctctacgactttcgtgattccgttccgcac
      M   S   G   L   K   K   F   F   P   Y   S   T   N   V  14
   1 ATG TCA GGG CTG AAG AAG TTC TTC CCT TAC AGC ACA AAC GTG
      L   K   G   A   A   A   D   I   A   L   P   S   L   A  28
  43 CTG AAG GGT GCT GCT GCG GAT ATC GCG CTC CCC TCG CTG GCG
      G   K   T   V   F   F   Y   F   S   A   S   W   C   P  42
  85 GGC AAG ACC GTA TTC TTC TAC TTC TCC GCG AGC TGG TGC CCG
      P   C   R   A   F   T   P   Q   L   I   E   F   Y   K  56
 127 CCG TGC CGG GCC TTC ACG CCG CAG CTG ATC GAT TTT TAC AAG
      A   H   A   E   K   K   N   F   E   V   M   L   I   F  70
 169 GCC CAC GCG GAG AAG AAG AAC TTC GAG GTG ATG CTC ATC TCC
      W   D   E   S   A   E   D   F   K   D   Y   Y   A   K  84
 211 TGG GAT GAG TCA GCA GAG GAC TTT AAG GAC TAC TAC GCG AAG
      M   P   W   L   A   L   P   F   E   D   R   K   G   M  98
 253 ATG CCG TGG CTG GCA TTG CCG TTT GAA GAC CGC AAA GGG ATG
      E   F   L   T   T   G   F   D   V   K   S   I   P   T 112
 295 GAG TTC TTG ACG ACC GGC TTC GAT GTG AAG TCG ATC CCA ACC
      L   V   G   V   E   A   D   S   G   N   I   I   T   T 126
 337 TTG GTG GGC GTC GAG GCG GAC TCG GGA AAC ATC ATC ACA ACG
      Q   A   R   T   M   V   V   K   D   P   E   A   K   D 140
 378 CAG GCG CGT ACG ATG GTG GTG AAG GAC CCG GAA GCA AAG GAT
      F   P   W   P   N   V   E   A   K   K   *             150
 421 TTT CCG TGG CCC AAC GTG GAG GCC AAG AAG TAA aggggagcgat
 466 tgagttgctgcaggcgtgcgtgaagcacctttatattttccttttcttctcct
 521 gtaggctgcgtg
```

Figure 3

```
                        ****  *  ****** ***********  *
TLP/CE        1    MSLLAGVKEEKRDKTLVDATEALAGKAVGFYFSAHWCPPCRGFTPILKDF    50
TXN (Tryp)                                        SLAGKLVFFYFSASWCPPCRGFTPQLIEF
TXN (Glu-C)                                                                  F

*                                     *
TLP/CE        51   YEEVEDEFEVVFVSFDRSESDLKMYMSEHGDWYHIPYGNDAIKELSTKYG   100
TXN (Tryp)         VDKFHESK                             MPWLAVPFAQSWAVQK  HFN
TXN (Glu-C)        VDKFHE

*  * *  *         *                 *
TLP/CE        101  VSGIPALIVKPDGTEVTKDGRNDVQNGKDPKATVAKWKA              140
TXN (Tryp)         VESIPTLIGVDADSGDVVTTR  ATLVKDPEGEQFPSKDA
TXN (Glu-C)            SIPTLIGVDADSGDVVTTRARAXLVK
```

Figure 7 kDa 67,0 →
43,0 →

30,0 →

20,1 →
14,4 →

1   2   3 kDa 67,0 →
43,0 →
30,0 →
20,1 →
14,4 →

1    2

US 6,432,671 B1

TRYPAREDOXIN, EXPRESSION PLASMID, PROCESS OF PRODUCTION, METHOD OF USE, TEST KIT, AND PHARMACEUTICAL COMPOSITION

This is a continuation of International Application No. PCT/EP97/06983 filed Dec. 12, 1997, the entire disclosure of which is incorporated herein by reference which claims priority to European Application Serial No. EPO 96120015.1, filed Dec. 12, 1996.

INTRODUCTION

Flagellated protozoan parasites of the family Trypanosomatidae are among the most prevalent human pathogens in tropical and subtropical areas. These organisms have complex life cycles and some of them are the causative agents of debilitating or life-threatening diseases, such as American Chagas' disease (*Trypanosoma cruzi*), African sleeping sickness (*T. brucei gambiense* and *T. b. rhodesiense*), oriental sore (*Leishmania tropica*), kala azar (*L. donovani*) and mucocutaneous leishmaniasis (*L. brasiliensis*). Others infect hosts as diverse as plants (Phytomonas species), insects (Crithidia and Leptomonas species) and livestock (*T. congolense*, *T. b. brucei*, *T. evansi*). Many of the human pathogens are also endemic in wildlife. Worldwide, more than 30 million people are estimated to suffer from trypanosomal and leislmanial infections (World Health Organisation, 1996). Vaccination strategies have so far failed and most of the chemotherapeutic drugs currently used for treatment are unsatisfactory in terms of both efficacy and toxicity (Risse, 1993). Nifurtimox, for instance, a drug widely used in the treatment of Chagas' disease, is an unspecific redox cycler affecting not only the peroxide sensitive parasites but also the host. Accordingly, the defense system against oxidants in the trypanosomatids, which differs substantially from the analogous host metabolism, has been discussed as a potential target area for the development of more specific trypanocidal agents (Fairlamb, 1996; Jacoby et al., 1996).

As parasites, the trypanosomatids are inevitably exposed to various reactive oxygen species, such as superoxide radicals, hydrogen peroxide and myeloperoxidase products, generated during the host defense reaction. However, their ability to cope with such oxidative stress appears to be surprisingly weak. Although they possess an iron-containing superoxide dismutase to scavenge phagocyte-derived superoxide (LeTrant et al., 1983), most of them lack both catalase and glutathione peroxidase (Docampo, 1990), the major hydroperoxide metabolising enzymes of the host organisms (Chance et al., 1979; Flohé, 1989). They also contain conspicuously low concentrations of glutathione (GSH), the major antioxidant sulfhydryl compound in mammalian cells. Instead they form a unique GSH derivative known as trypanothione ($T(SH)_2$; $N^1,N^8$-bis(glutathionyl)spermidine) (FIG. 1), which is believed to play a central role in their antioxidant defense system (Fairlamb et al., 1985; Fairlamb and Cerami, 1992). $T(SH)_2$ can be oxidized by $H_2O_2$ to the corresponding cyclic disulphide ($TS_2$) (FIG. 1) and is regenerated at the expense of NADPH by trypanothione reductase (TR; Bailey et al., 1993; Jacoby et al., 1996) (FIG. 1). Whether the reaction of $T(SH)_2$ with $H_2O_2$ is enzymatically catalyzed has, however, been the subject of debate. A $T(SH)_2$-dependent peroxidase activity was repeatedly reported for crude extracts of the trypanosomatids (Penketh and Klein, 1986; Henderson et al., 1987; Penketh et al., 1987). However, a pertinent enzymatic entity could never be purified (Henderson et al., 1987; Penketh et al., 1987) and doubts about its existence were raised (Penketh and Klein, 1986). A recent systematic investigation of the various developmental stages of *T. cruzi* even concluded that non-enzymatic oxidation of $T(SH)_2$ by $H_2O_2$ may fully account for the slow hydroperoxide metabolism in this species (Carnieri et al., 1993).

The present invention is based on the discovery that hydroperoxide metabolism in the trypanosomatids is enzymatic in nature, but distinct from any known metabolic pathway of the host organisms (Nogoceke et al., 1997). Apart from the previously known trypanothione reductase (TR), the parasitic pathway comprises two novel proteins, called tryparedoxin (TXN) and tryparedoxin peroxidase (TXNPx), which together catalyse the reduction of hydroperoxides at the expense of NADPH as depicted in FIG. 1. Isoforms of tryparedoxin exist in one species.

The uniqueness of this cascade of oxidoreductases offers the possibility to inhibit the parasitic metabolism without causing adverse effects in the host organism.

Thus, one embodiment of the invention concerns proteins, which we called tryparedoxins (trypanothione: peroxiredoxin oxidoreductases) and which are characterized by their capability of transferring reductive equivalents of trypanothione to a peroxiredoxin-type protein such as tryparedoxin peroxidase. As regards peroxi-redoxins and peroxi-redoxin-type proteins, reference is made to Chae et al. in J. Biol. Chem., 269(1994) 27670–24678 and in PNAS USA, 91 (1994) 7017–7021 and to EP 96 120 016.9 or PCT/EP 97/04 990. Tryparedoxins exhibit a catalytic site similar to that of thioredoxin, an ubiquituous redox mediator with pleiotropic functions. Typical thioredoxins have never been found in any trypanosomatid. It therefore appears conceivable that in the trypanosomatids the tryparedoxins substitute for thioredoxin in such diverse metabolic functions as reduction of ribonucleotides, differentiation, regulation of transcription or other regulatory processes depending on the cellular thiol/disulphide equilibrium. The possibility of multiple biological functions of tryparedoxins is further suggested by the coexistence of more than one tryparedoxin in the same species, as described below.

The proteins according to the invention can be characterized in that they can be prepared by means of and/or isolated from a species of the family Trypanosomatidae.

Further, the proteins according to the invention can be characterized in that their preparation and/or isolation can be carried out by genetic engineering, especially by means of an oligonucleotide as probe having the oligonucleotide sequence of SEQ ID NO: 5 and encoding the amino acid sequence of SEQ ID NO: 4 (FIG. 2) or any useful part thereof.

Further, the proteins according to the invention can be characterized by a molecular weight of 15–19 kDa.

Further, a protein according to the invention can be characterized by a WCPPC motif and catalyzing the reduction of protein disulphide bonds by means of trypanothione.

Further, a protein according to the invention can be a protein (a) having the amino acid sequence SEQ ID NO: 6 (FIG. 3, positions 1 to 150) or
(b) having an amino acid sequence which is homologous to said according to (a), has the same number or a smaller or slightly smaller or larger number of amino acids than SEQ ID NO: 6 and is encoded by an oligonucleotide which is hybridizable with an oligonucleotide which encodes a protein comprising or having the amino acid sequence SEQ ID NO: 4 or SEQ ID NO: 6.

Further, the protein according to (b) can be a protein having an amino acid sequence which is homologous to SEQ ID NO: 4 or SEQ ID NO: 6 by at least 70% and especially at least 75%.

Another embodiment of the invention concerns plasmids for the expression of proteins according any of the preceding claims and comprising a nucleic acid sequence encoding said proteins.

The plasmids according to the invention may comprise DNA sequences encoding tryparedoxin especially of *Crithidia fasciculata*.

Further, a plasmid according to the invention may comprise a DNA sequence encoding functionally active derivatives of tryparedoxin designed for the isolation in a manner known per se.

Further, a plasmid according to the invention may comprise a DNA sequence encoding functionally active derivatives of tryparedoxin wherein the tryparedoxin is derivatised by a His tag.

Still another embodiment of the invention concerns a process for the production of a protein according to the invention characterized in that it is produced by means of a DNA sequence encoding the amino acid sequence of SEQ ID NO: 6 by genetic engineering in a manner known per se.

The process according to the invention can be characterized in that the production is carried out by means of a plasmid according to the invention.

Further, the process according to the invention can be characterized in that the host is selected from the group consisting of bacteria, fungi, yeast, plant cells, insect cells, mammalian cells and cell cultures (heterologous expression).

Further, the process according to the invention can be characterized in that *Escherichia coli* is used as host.

Still another embodiment of the invention concerns the use of a protein according to the invention for testing and recovering inhibitory substances which inhibit activities of said protein.

Still another embodiment of the invention concerns a test system for testing the catalytic activity of a protein according to the invention or obtained according to the process according to the invention, wherein the testing system contains or comprises trypanothione, trypanothione reductase, a tryparedoxin peroxidase, a tryparedoxin and, in addition, a hydroperoxide as indicator enzyme, mediator and substrate, respectively.

Finally, another embodiment of the invention concerns a pharmaceutical preparation having a trypanocidal activity and comprising an inhibitory substance inhibiting the catalytic activity of a protein according to the invention or of a protein which can be obtained according to the process according to the invention.

The pharmaceutical composition according to the invention can be characterized in that it can be obtained by a use according to the invention and by using a test system according to the invention.

BRIEF DESCRIPTION OF DRAWINGS

The invention is now described in greater detail by means of figures and examples.

FIG. 2 Nucleotide sequence (SEQ ID NO: 5) and deduced amino acid sequences (SEQ ID NO: 4) of the PCR product used to screen a genomic library for inserts containing the tryparedoxin I gene. Partial sequences confirmed by protein sequence analysis are underlined and the sequences corresponding to the primers used to obtain the PCR product are double underlined.

FIG. 3 Nucleotide (SEQ ID NOs: 7, 8) and amino acid (SEQ ID NO: 6) sequences of tryparedoxin II isolated from a *C. fasciculata* genomic library. The start and stop codons are in bold. The position of the Pvu II site from which one third of the gene at the 5' end of the open reading frame was determined is double underlined. The WCPPC thioredoxin-like motif is underlined.

FIG. 7 Sequence alignment of the peptide fragments of tryparedoxin I (Txn, SEQ ID NOs: 10–15) with thioredoxin-like protein of *Caenorhabditis elegans* (TLP/CE SEQ ID NO: 9). Tryparedoxin I was digested with trypsin (Tryp SEQ ID NOs: 10–13) or endoproteinase Glu-C (Glu-C SEQ ID NOs: 14–15). Asterisks denote conserved residues.

EXAMPLE 1

Isolation of tryparedoxin from *C. fasciculata*

*C. fasciculata* was cultivated in a 100 l fermenter as described (Shim and Fairlamb, 1988). The cells were harvested in the late log phase, suspended in 50 mM sodium phosphate pH 5.8 (buffer B) containing 0.1 mM PMSF, then frozen and thawed twice to complete cell disruption. Cell debris was removed by centrifugation at 25,000×g for 30 min and the supernatant was applied on an S-Sepharose column pre-equilibrated with buffer B. Tryparedoxin peroxidase eluted at 150 mM NaCl in buffer B and was directly loaded on a hydroxyapatite (BioRad, USA) column pre-equilibrated with 10 mM sodium phosphate pH 6.8. Tryparedoxin peroxidase was eluted stepwise with 0.4 M potassium phosphate pH 6.8. The protein was extensively dialyzed against 20 mM Tris pH 7.6 (buffer C) and purified to homogeneity on a Resource Q column, eluting at 0.1 M NaCl in buffer C. The flow-through of the S-Sepharose column containing trypanothione reductase and tryparedoxin can be used to measure the enzymatic activity of tryparedoxin peroxidase (see example 2). The flow-through of the S-Sepharose column, containing trypanothione reductase and tryparedoxin, was adjusted to pH 7.2 with 1 M NaOH. The extract was adjusted to 3% (w/v) streptomycin sulphate, brought to 50% ammonium sulphate saturation, and centrifuged for 10 min at 11,000×g. The supernatant was adjusted to 80% ammonium sulphate saturation and recentrifuged. The pellet was dissolved in, then dialyzed extensively, against 20 mM bis-Tris propane pH 7.2 containing 1 mM EDTA and 1 mM DTT (buffer D). The enzyme extract was loaded on a DEAE-Sepharose column and eluted with a linear gradient of 0.4 M KCl in buffer D. The sample eluting at 80–120 mM KCl was concentrated by ultrafiltration (Omegacell, Filtron, Germany), washed with 20 mM potassium phosphate pH 7.2 containing 1 mM EDTA and 1 mM DTT (buffer E) and loaded on a 2'5'ADP-Sepharose 4B column. Trypanothione reductase was eluted with 5 mM NADP in buffer E and purified to homogeneity on a Sephacryl S-200 column. The unbound fraction was concentrated by ultrafiltration and fractionated on an Ultrogel AcA54 (LKB, Sweden) gel filtration column in 50 mM Hepes pH 7.6 containing 150 mM NaCl, 1 mM EDTA and 1 mM DTT to yield homogeneous tryparedoxin. The authentic tryparedoxin, thus isolated, is termed tryparedoxin I (TXN I). The overall yields of the final purification scheme are shown in Table 1.

TABLE 1

Yields and purification factors during the isolation of tryparedoxin I.

|  | Volume (ml) | Activity (U) | Protein (mg) | Yield U/mg | cation (%) | Purification factor |
|---|---|---|---|---|---|---|
| Cell extract | 180 | 386 | 3322 | 1e + 10 | (100) | (1.0) |
| (NH$_4$)$_2$SO$_4$ precipitation | 86 | 134 | 1728 |  | 35 | 0.7 |
| DEAE-Sepharose | 270 | 136 | 176 |  | 36 | 6.4 |
| Ultrogel AcA54 | 13 | 51 | 22 |  | 13 | 20.2 |

Figure 1:
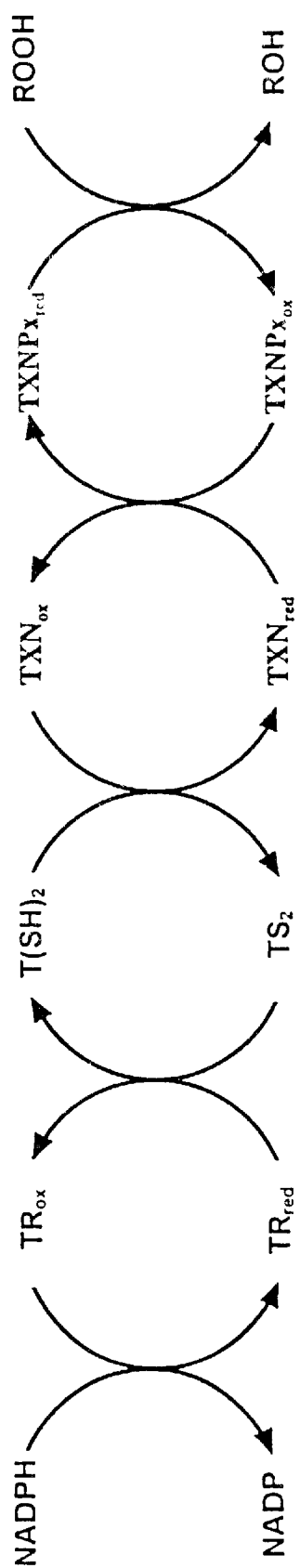
FIG. 1 Flux of reducing equivalents from NADPH to hydroperoxide in *C. fasciculata*. TR=trypanothione reductase; $T(SH)_2$=trypanothione; $TS_2$=trypanothione disulphide; TXN=tryparedoxin; TXNPx=tryparedoxin peroxidase; ROOH=hydroperoxide.
Figure 4:
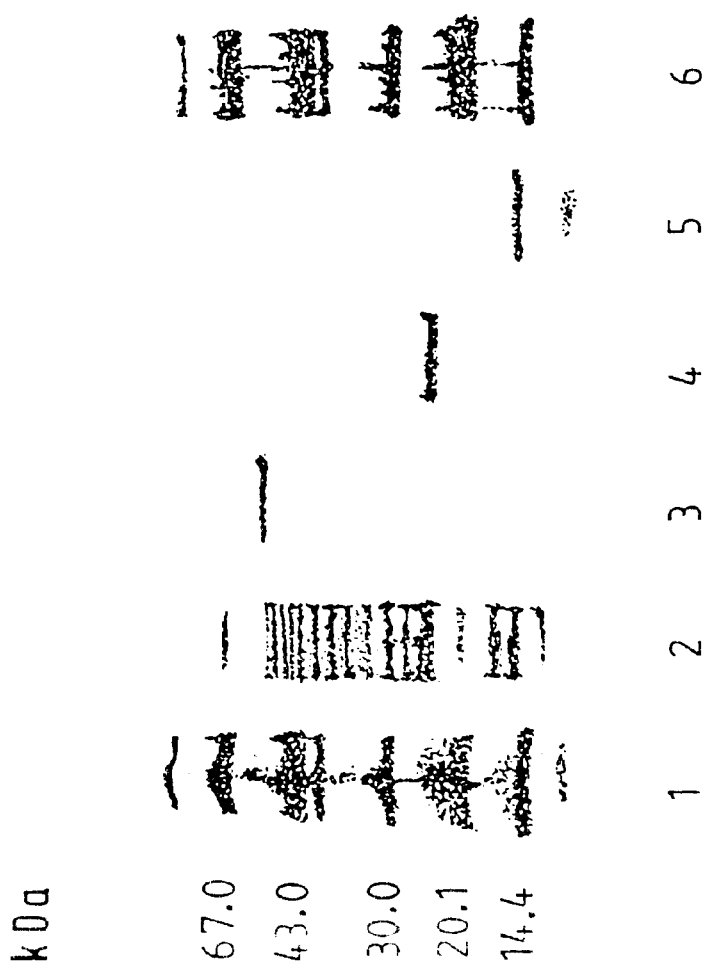
FIG. 4 Components of the trypanothione-mediated hydroperoxide metabolising system from *C. fasciculata* in silver-stained SDS-PAGE (8–25%). Lane 2, extract of disrupted cells; lane 3, trypanothione reductase; lane 4, tryparedoxin peroxidase and lane 5, tryparedoxin I. Lanes 1 and 6, molecular weight standards.
Figure 5:
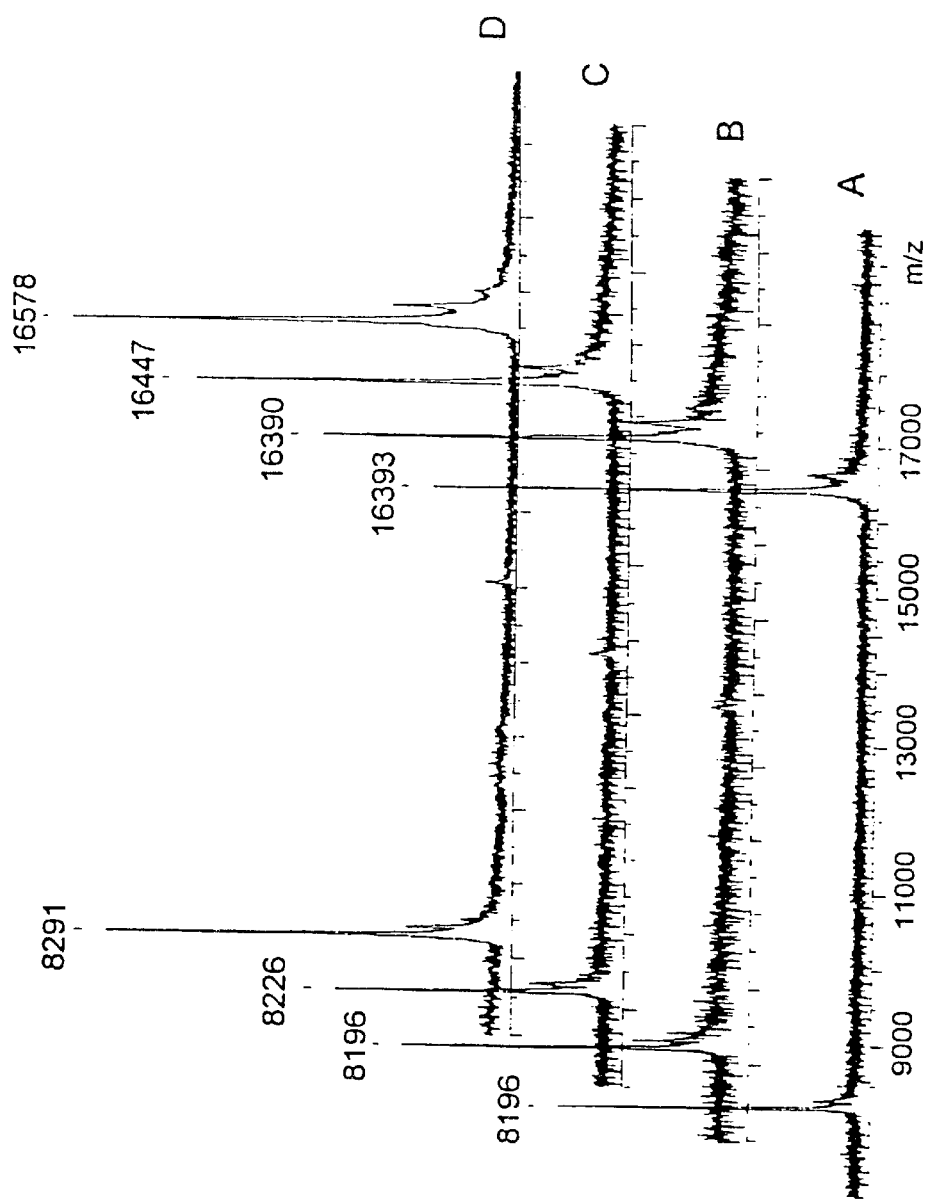
FIG. 5 Molecular mass determination by MALDI-TOF of pure tryparedoxin I from *C. fasciculata* (trace A), tryparedoxin I exposed to iodoacetarmide (trace B), $T(SH)_2$-reduced tryparedoxin I derivatized with iodoacetamide (trace C) and with iodoacetamide plus N-ethylmaleimide (trace D). The mass increments shown in traces C and D correspond to the addition of one carboxyamidomethyl residue (observed 54 Da, theoretical 57 Da) and one carboxyamidomethyl plus one N-ethylsuccinimide residue (observed 185 Da, theoretical 182 Da), respectively.

Based on the purification factors yielding homogeneous products the minimum concentrations of tryparedoxin and tryparedoxin peroxidase in the starting material were estimated to amount to 5% and 6% of the total soluble protein, respectively. The homogeneity and approximate molecular masses of the purified proteins are shown in FIG. 4. The apparent subunit masses deduced by SDS-PAGE (about 16000) were compatible with those obtained by MALDI, 16393±10 (FIG. 5). Analyses of the spectral properties of the two proteins confirmed the absence of any chromophoric cofactors absorbing in the visible region.

EXAMPLE 2

Determination of Tryparedoxin Activity

In essence, the activity of tryparedoxin activity is measured by coupling the catalytic reduction of hydroperoxide mediated by tryparedoxin peroxidase to NADPH consumption by means of trypanothione and trypanothione reductase. For example, an assay sample may contain 0.1 mM NADPH in 50 mM Hepes pH 7.6, 1 mM EDTA, 50 M $H_2O_2$ or t-butyl hydroperoxide (t-bOOH), 45 M T(SH)$_2$, 16.5 µg/ml tryparedoxin peroxidase and 0.34 U trypanothione reductase and an unknown amount of tryparedoxin. Unless otherwise stated, the reaction is started with the addition of the hydroperoxide. Dihydro-trypanothione is obtained by chemical reduction of TS$_2$ (Bachem, Switzerland) as described (Fairlamb et al., 1986). t-BOOH may be replaced by other hydroperoxides, such as $H_2O_2$, linoleic acid hydroperoxide or phosphatidylcholine hydroperoxide.

Figure 6:
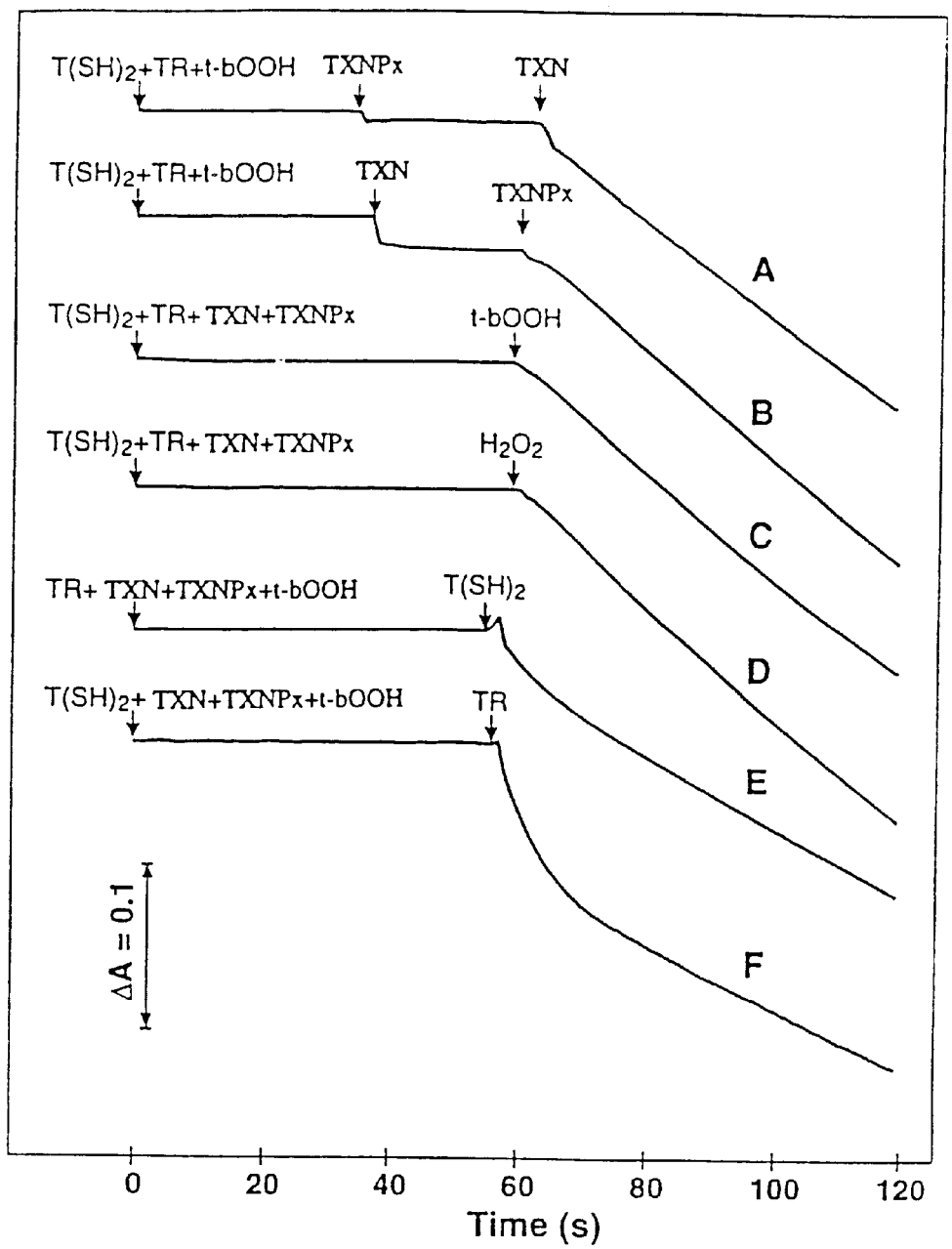
FIG. 6 NADPH-dependent hydroperoxide metabolism reconstituted from components isolated from *C. fasciculata*. Peroxidase activity depends on both isolated proteins, tryparedoxin I (TXN I) (A) and tryparedoxin peroxidase (TXNPx) (B), as well as $T(SH)_2$ (E) and trypanothione reductase (TR) (F). The comparatively high activity in (F) observed immediately after the addition of TR is due to the accumulation of its substrate, $TS_2$. Note that the reaction is comparably fast with $H_2O_2$ (D) and t-bOOH (C). The tests were performed at 27° C. with 0.1 mM NADPH, 16.5 µg/ml tryparedoxin peroxidase, 12 µg/ml tryparedoxin I, 45 µM $T(SH)_2$, 45 µM hydroperoxide and 0.4 U/ml TR. NADPH consumption was measured photometrically at 340 nm.

FIG. 6 demonstrates that trypanothione reductase, T(SH)$_2$, tryparedoxin and tryparedoxin peroxidase are indispensable for the efficient reduction of $H_2O_2$ or alkyl hydroperoxides by NADPH, The T(SH)$_2$-mediated "NADPH peroxidase activity" of *C. fasciculata* is thus achieved by the concerted action of three distinct proteins; the well characterized trypanothione reductase (Bailey et al., 1993), tryparedoxin and tryparedoxin peroxidase.

EXAMPLE 3

Characterisation of Tryparedoxin I by Partial Proteins Sequencing

Since the N-terminus of tryparedoxin I was blocked, the protein was digested with either bovine trypsin or endoproteinase Glu-C from *Staphylococcus aureus* (both sequencing grade, Promega) according to Stone and Williams (1993). The peptides were separated by HPLC (Applied Biosystems 172A) on an Aquapore OD-300 RP-18 column. Automated Edman degradation was performed with an Applied Biosystems, Inc. sequencer with an on-line C-18 reverse phase HPLC. Database searches were performed with the BLAST and FASTA programs. Peptides were aligned with the Bestfit program, Genetics Computer Group (GCG), Madison, Wis., USA.

Seven fragments could be sequenced and could be aligned to a thioredoxin-like protein of *C. elegans* (FIG. 7).

EXAMPLE 4

Use of Sequenced Fragments of Tryparedoxin I to Elucidate the Encoding DNA

Cells culture and DNA extraction

*C. fasciculata* (HS6) was grown as described by Shim and Fairlamb (1988). The cells were harvested by centrifugation for 15 min at 7000 rpm, washed twice with saline solution (0.9% NaCl) and resuspended in 5 ml buffer (50 mM TrisHCl, 100 mM EDTA, 15 mM NaCl, 0.5% SDS, 100 $\mu$g ml$^{-1}$ Proteinase K, pH 8.0). Resuspended cells were preincubated at 50° C. for 40 min. The genomic DNA was extracted twice with equivalent volumes of phenol (incubation: 60° C. for 45 min; centrifugation: 20 min, 4500 rpm) followed by phenol:chloroform:isoamyl alcohol (25:24:1) and chloroform:isoamyl alcohol extraction (24:1). Genomic DNA was precipitated with sodium acetate and ethanol.

Primers, hybridization probes and sequence analysis: Based on the peptide sequences of tryparedoxin I (Nogoceke et al., 1997) degenerate oligodeoxyribonucleotides were synthesized. Polymerase chain reaction (PCR) amplification was performed using the GeneAmp PCR Core kit (Perkin Elmer) using 0.2 $\mu$g of *C. fasciculata* genomic DNA as template, 5 $\mu$l of 10× reaction buffer, 3 $\mu$l 25 mM MgCl$_2$, 1 $\mu$l of each 10 $\mu$M dNTP, 100 pmol of each primer and 0.25U Taq polymerase. An annealing temperature of 52° C. was used. The PCR product was analysed by agarose gels and purified using the QIAquick PCR purification kit (QIAGEN Inc.). Sequencing was performed on a 373A DNA Sequencer (Applied Biosystems) using the PRISM Ready Reaction DyeDeoxy Terminator Sequencing Kit (1550V, 19 mA, 30 W, 42° C.). When used as a hybridization probe the PCR product was labelled with digoxigenin using the DIG DNA Labeling Kit (Boehringer Mannheim) according to the instructions provided by the supplier.

Library construction and screening procedure: The genomic DNA was partially digested for 5–30 min with a ratio unit Sau3A/$\mu$g DNA of 0.005. The efficiency of the digestion was monitored by electrophoresis on agarose gels. Proteins were removed from the DNA using StrataClean Resin (Stratagene). The Sau3A sites were partially refilled with dATP and dGTP and Klenow fragment. The genomic DNA was ligated into Lambda GEM-11 Xho I half site arms (Promega) at a molar ratio of DNA to genomic DNA (average size 15 kb) of 1:0.7. The ligated DNA was packaged using the Packagene Lambda DNA Packaging System (Promega) according to the suppliers' instructions. The phages were used to infect the *E. coli* host strain LE392 (Promega) according to the standard protocol. 5.1×10$^3$ pfu of the genomic library were plated on agar. The plaques were transferred to 9 cm diameter Biodyne-A nylon membranes and screened with the DIG-labelled PCR probes following the instructions provided by the supplier but using a hybridization temperature of 54 C. DIG labelled nucleic acids were detected calorimetrically with the DIG Nucleic Acid Detection Kit (Boehringer Mannheim). Positive clones were rescreened, amplified and suspended in SM buffer. The phages were precipitated by PEG 8000 and purified in CsCl gradients. The isolated DNA was used for restriction analyses ( Sac I, EcoR I, BamH I, Xho I, Nco I) or as template for PCR reactions. The digestion products were eluted from agarose gels and ligated into pBluescript II KS (+/−) phagemids (Stratagene) or pET24d(+) vector (Novagen). The ligated DNA was used to transform *E. coli* LE392. Transformed cells were selected by ampicillin (pBluescript II KS (+/−) phagemid) or kanamycin (pET24d(+) vector) resistance, plasmids were purified using QIAprep Spin Plasmid Kit (Qiagen Inc.) and analyzed by restriction enzyme digestion and sequencing.

Isolation and sequencing of tryparedoxin genes from *C. fasciculata*: Sequenced peptide fragments obtained from isolated tryparedoxin I of *C. fasciculata* (Nogoceke et al., 1997) could be aligned along the established deduced amino acid sequence of a thioredoxin-like protein of *Caenorhabditis elegans*. This enabled appropriate degenerate PCR primers to be designed for the generation of a PCR product from the *C. fasciculata* genomic DNA. This PCR product, which coded for approximately the 50% of tryparedoxin I (FIG. 2), was subsequently used to screen a genomic library for inserts containing the full length DNA encoding tryparedoxin I. A clone containing a 22 kb insert with the presumed tryparedoxin I gene was isolated. The DNA was digested with the restriction enzyme Sac I to separate the phage arms from the insert and with the restriction enzyme Nco I. A southern blot was performed and a fragment of 6 kb hybridized with the labelled PCR product. The fragment was subcloned into the pET24d(+) vector (Novagen). Subsequent digestion of the cloned fragment with the restriction enzyme Pvu II led to the isolation and cloning of a 1 kb fragment. When this fragment was sequenced it contained only one third of the gene coding for tryparedoxin at the 5' end of the open reading frame (FIG. 3). The DNA sequence thus obtained was in full agreement with the peptide sequence derived from the isolated tryparedoxin I.

EXAMPLE 5

Isolation of a New Tryparedoxin Gene (TXN II)

New primers were designed using the information obtained in example 4 and the complete gene was sequenced directly from the 6 kb fragment. The previously obtained PCR product is about 60% identical in its amino acid sequence to the correponding region of the isolated gene. The full length encoding DNA and the deduced amino acid sequence are shown in FIG. 3. The gene encodes for a protein with a molecular mass of 17000, while the molecular mass of natural tryparedoxin I isolated from *C. fasciculata* is 16393±10 (Nogoceke et al.,1997).

EXAMPLE 6

Heterologous Expression of tryparedoxin II in *Escherichia coli*

The tryparedoxin gene contained in the cloned 6 kb fragment was amplified by PCR with a forward primer A (5'-TCGTGATTCCGTTCCGCATATGTCAGGGC-3') (SEQ ID NO: 1) that contains an Nde I site and overlaps the 5' end of the coding sequence, and a reverse primer B (5'-GCAACTCAATCGCTCCCCTCGAGCTTCTTGGCC TCC-3') (SEQ ID NO: 2) which overlaps the 3' end of the coding sequence and contains an Xho I site. Consequently a leucine and a glutamate residue are added, the stop codon is deleted and the protein will contain 6 histidine residues at its carboxyl-terminal end. Amplification was performed as above but using the Expand High Fidelity polymerase mixture and buffer (Boehringer Mannheim) at an annealing temperature of 50° C. with the extension temperature being increased in 10 sec increments per cycle during cycles 10–20. The amplified coding region was digested with Nde I and Xho I and ligated to a pET24a(+) vector (Novagen) treated with the same enzymes and dephosphorylated. The resulting plasmid (pET/TXN II H6) was used to transform *E. coli* BL21(DE3). Transformed cells were selected by kanamycin resistance, the plasmids purified and sequenced.

The same procedure, but using a reverse primer C (5'-CAGCAACTCAATGGATCC TCATTACTTCTTGGCC-3') (SEQ ID NO: 3) instead of reverse primer B, was used to express tryparedoxin II with no changes at the carboxyl-terminal end. In this case the reverse primer contained an extra stop codon and a BamH I site at the 5'-end of the extra stop codon, with the digestions for the cloning step being performed with Nde I and BamH I. The resulting plasmid was called pET/TXN II and was used to transform *E. coli* BL21(DE3). Transformed cells were selected by kanamycin resistance, the plasmids purified and sequenced.

Figure 8:
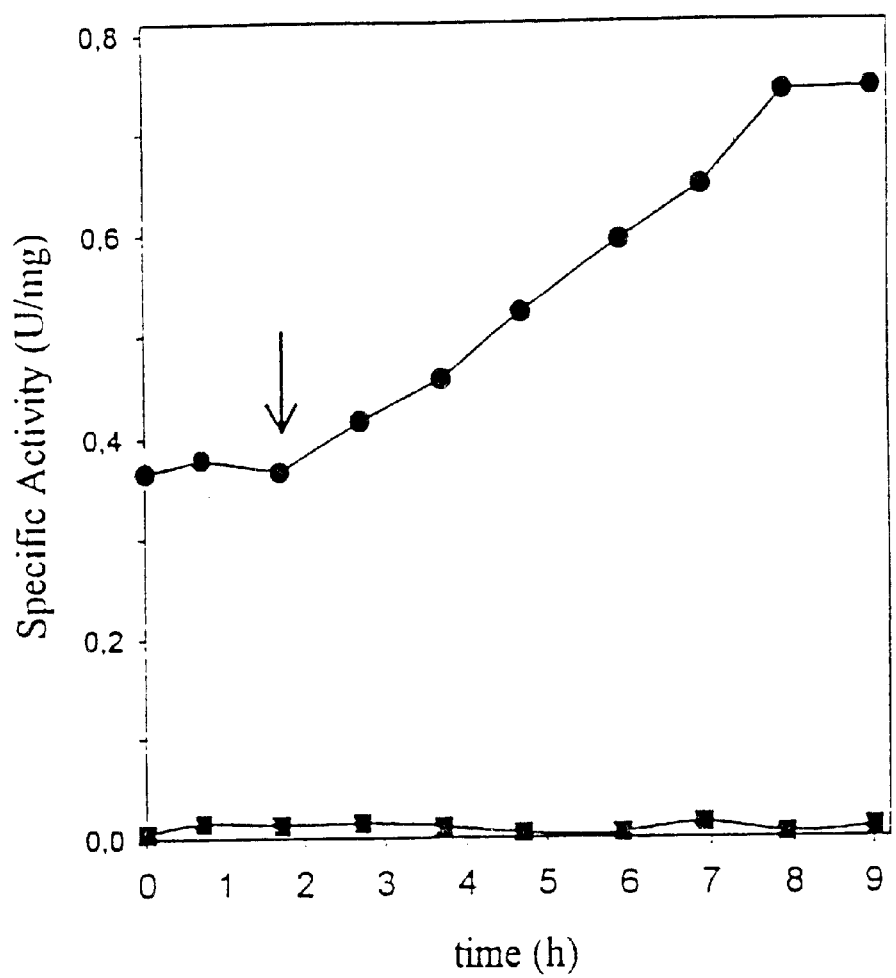
FIG. 8 Tryparedoxin II containing a His tag specific activity determined in the supernatants of sonicated *E.coli* BL21(DE3)pET24a cells (black square) and *E. coli* BL21 (DE3)pET/TXN II H6 cells (black circle). Gene expression induction by isopropyl-β-D-thiogalactopyranoside addition is indicated by an arrow.
Figure 9:
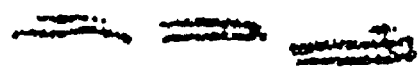
FIG. 9 Western blot analysis of expressed tryparedoxin II containing a His tag. SDS-PAGE was done under reducing conditions in 8–25% gradient gels on a Pharmacia Phast System and the samples were electroblotted onto a PVDF membrane using a Pharmacia Phast System. Whole rabbit serum (1:500 dilution) containing antibodies raised against pure *C. fasciculata* tryparedoxin I was used as primary antibody and anti-rabbit goat antibodies (Sigma) as secondary antibody. Lane 1, supernatant of *E. coli* BL21(DE3) pET/TXN II H6 cells 6 h after induction; lane 2, purified recombinant tryparedoxin II; lane 3, authentic tryparedoxin I from *C. fasciculata*.

*E. coli* BL21(DE3) pET/TXN IIH6 were grown to $A_{600}$ of 0.9–1.0 at 25° C. and 180 rpm in LB medium with 30 kg kanamycin/ml, then expression of the tryparedoxin II gene was induced with 1 mM isopropyl--D-thiogalactopyranoside. *E. coli* BL21(DE3) containing the pET24a plasmid was grown in the same way. Samples taken at different times were centrifuged, resuspended in 50 mM Tris-HCl pH 8.0, 1 mM EDTA buffer, sonicated and centrifuged. Enzyme activity was determined as in Nogoceke et al. (1997); protein concentration was determined using Coomassie Brilliant Blue-G reagent (BioRad) with bovine serum albumin as standard. After induction of the transformed bacteria, a marked increase in tryparedoxin activity was detected in supernatants of sonicated cells. Activity increased to a maximum 6 hours after induction and no activity was found in the control (FIG. 8). Induction resulted in the accumulation of a new protein with an apparent molecular mass of 18000, which was recognised by the anti-tryparedoxin antibodies raised against pure *C. fasciculata* tryparedoxin I (FIG. 9).

Figure 10:
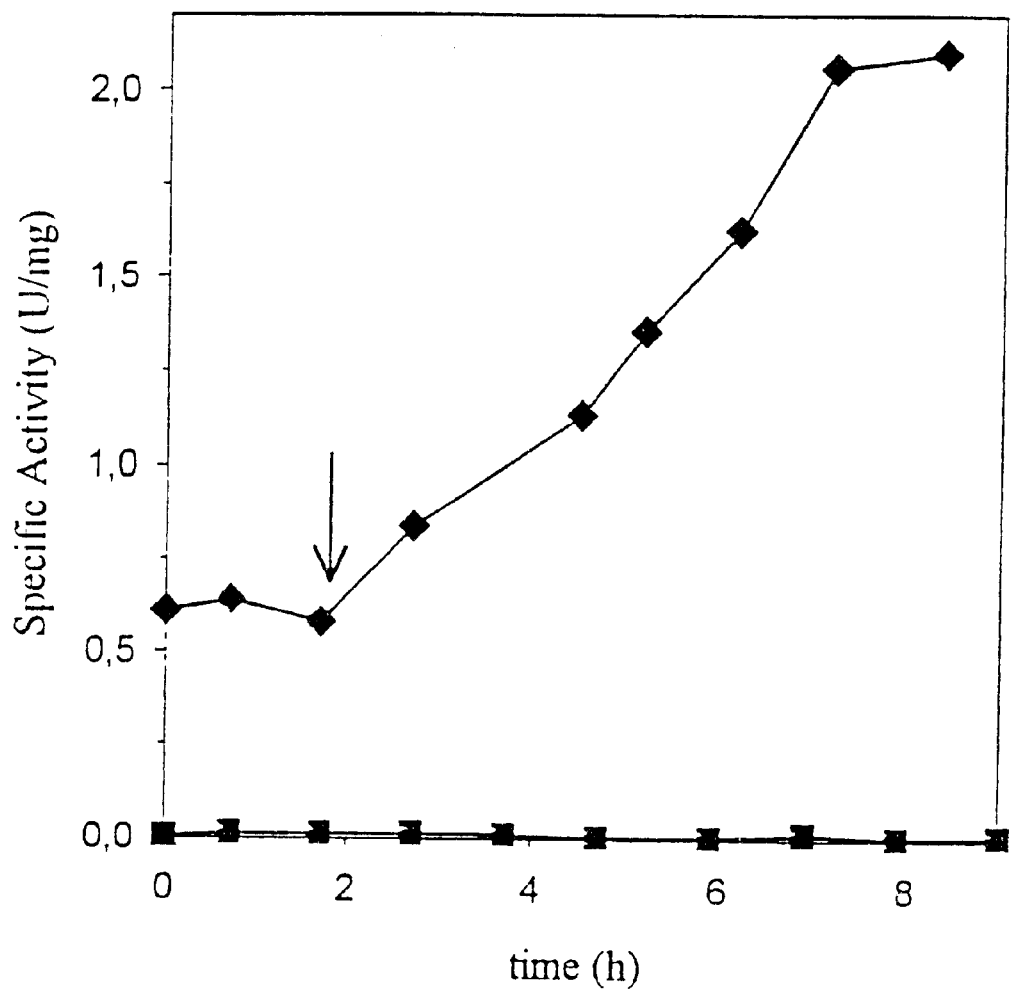
FIG. 10 Tryparedoxin II specific activity determined in the supernatants of sonicated *E.coli* BL21(DE3)pET24a cells (black square) and *E.coli* BL21(DE3)pET/TXN II cells (black rhomb). Gene expression induction by isopropyl-β-D-thiogalactopyranoside addition is indicated by an arrow.
Figure 11:
FIG. 11 Western blot analysis of expressed tryparedoxin II. SDS-PAGE was done under reducing conditions in 8–25% gradient gels on a Pharmacia Phast System and the samples were electroblotted onto a PVDF membrane using a Pharmacia Phast System. Whole rabbit serum (1:500 dilution) containing antibodies raised against pure *C. fasciculata* tryparedoxin I was used as primary antibody and anti-rabbit goat antibodies (Sigma) as secondary antibody. Lane 1, authentic tryparedoxin I from *C. fasciculata;* lane 2, supernatant of *E. coli* BL21(DE3) pET/TXN II cells 6 h after induction.

*E. coli* BL21(DE3) pET/TXN II were grown to $A_{600}$ of 0.9–1.0 at 25° C. and 180 rpm in LB medium with 30 kg kanamycin/ml, then expression of the tryparedoxin II gene was induced with 1 mM isopropyl-D-thiogalactopyranoside. *E. coli* BL21(DE3) containing the pET24a plasmid was grown in the same way. Samples taken at different times were centrifuged, resuspended in 50 mM Tris-HCl pH 8.0, 1 mM EDTA buffer, sonicated and centrifuged. Enzyme activity was determined as in Nogoceke et al. (1997); protein concentration was determined using Coomassie Brilliant Blue-G reagent (BioRad) with bovine serum albumin as standard. After induction of the transformed bacteria, a marked increase in tryparedoxin activity was detected in supernatants of sonicated cells. Activity increased to a maximum 6 hours after induction and no activity was found in the control (FIG. 10). Induction resulted in the accumulation of a new protein with an apparent molecular mass of 18000, which was recognised by the anti-tryparedoxin antibodies raised against pure *C. fasciculata* tryparedoxin I (FIG. 11)

EXAMPLE 7

Purification and Characterization of Recombinant Tryparedoxin II

Figure 12:
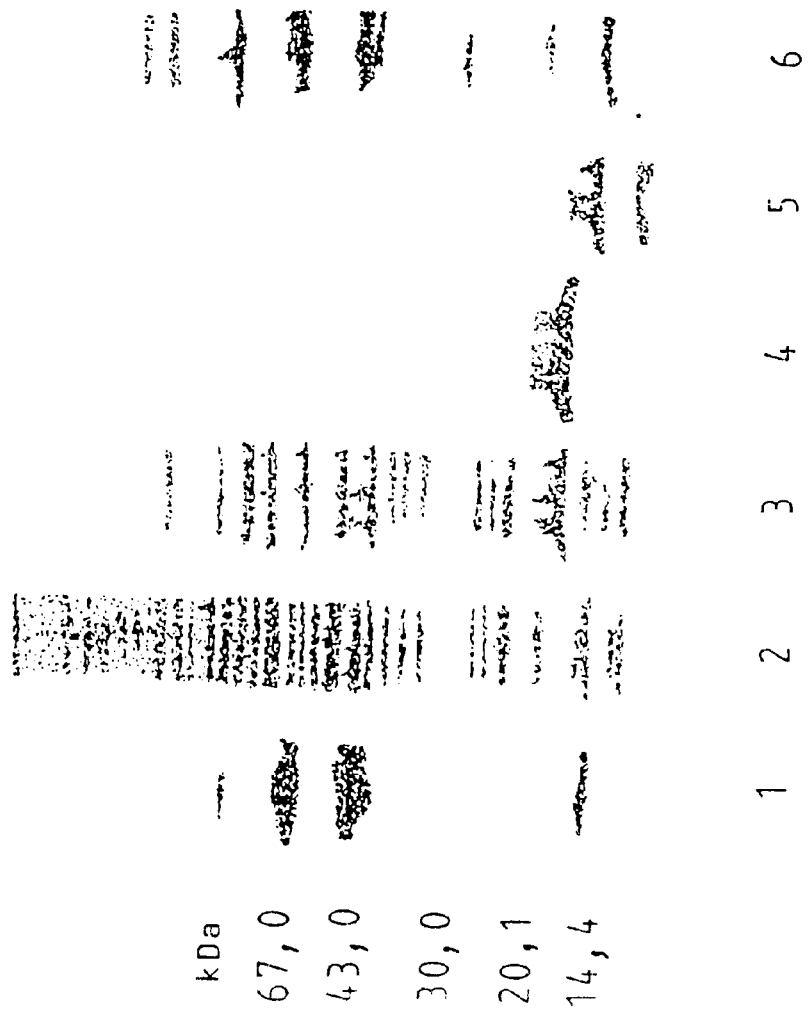
FIG. 12 SDS-PAGE of expressed tryparedoxin II containing a His tag. SDS-PAGE was done under reducing conditions in 8–25% gradient gels on a Pharmacia Phast System and the gels were stained for protein with silver according to the manufacturers' recommendations. Lane 2, supernatant of *E. coli* BL21(DE3) pET24a cells after 6 h induction; lane 2, supernatant of *E. coli* BL21(DE3) pET/TXN II H6 cells 6 h after induction; lane 3, purified recombinant tryparedoxin II; lane 4, authentic tryparedoxin I from *C. fasciculata*. Lanes 1 and 6, molecular weight standards.

*E. coli* BL21(DE3) pET/TXN II H6 was grown at 25° C. and 180 rpm in LB medium with 30 µg kanamycin/ml to $A_{600}$ of 0.9–1.0, then expression of the tryparedoxin II gene was induced with 1 mM isopropyl-D-thiogalactopyranoside. After 6 h the culture was centrifuged and either stored at −20° C. or the cells were resuspended in 0.05 culture volumes of binding buffer (5 mM imidazole, 500 mM NaCl and 20 mM Tris-HCl pH 7.9). The cell suspension was sonicated on ice and centrifuged for 40 min at 4° C., 13000 rpm. The supernatant was applied to a His Bind resin (Novagen) column charged with $Ni^{2+}$ and equilibrated with binding buffer, at a flow rate of about 10 column volumes per hour. The column was washed with 10 volumes of binding buffer and 6 volumes of 500 mM NaCl, 20 mM Tris-HCl pH 7.9 buffer containing 100 mM imidazole. Tryparedoxin eluted in the buffer containing 500 mM imidazole. Active fractions were pooled and immediately dialysed against 50 mM Tris-HCl pH 7.6 buffer containing 1 mM DTT and 1 mM EDTA. Tryparedoxin II eluted at 500 mM imidazole and was shown to be pure by SDS-PAGE and subsequent silver staining (FIG. 12). N-terminal sequencing of this protein showed the initial methionine to be missing and allowed us to confirm the first 20 amino acids. The expressed tryparedoxin II showed a molecular mass of about 18000 in SDS-PAGE (FIG. 12 ), being slightly bigger than the authentic tryparedoxin I. The difference in the molecular mass between the recombinant and authentic tryparedoxin peroxidase corresponded mainly to the additional amino acids (leucine, glutamate and 6 histidine residues) added at the C-terminal end of the recombinant enzyme.

The purified recombinant enzyme had a specific activity of 7.7 U/mg compared to 2.3 U/mg for the authentic enzyme.

EXAMPLE 8

Inhibition Studies

The test system described in example 2 is easily adapted to screen compounds for specific inhibition of tryparedoxin I. As an example the inhibition of tryparedoxin peroxidase by S-modifying agents such as N-ethylmaleimide (NEM), iodoacetamide (IAM) and phenylarsine oxide (PAO) is described (Table 2). Tryparedoxin was preincubated in 50 mM Hepes, 1 mM EDTA, pH 7.6 with or without presumed reducing substrate ($T(SH)_2$), then reacted with inhibitors and activity was checked at 22° C. essentially as described in example 2. Changes in molecular mass were determined by MALDI-TOF-MS (FIG. 5).

TABLE 2

Derivatisation scheme of tryparedoxin.

| Protein | Pretreatment | Derivatisation | mass increment[b] | residual activity [%] |
|---|---|---|---|---|
| tryparedoxin (9.5 µM) | 1.16 mM T(SH)$_2$; 15 min at 22° C. | — | — | ~100 |
| | none[a] | 3 mM IAM; 30 min at 220° C. | 4 ± 3 (0) | 83 ± 5 |
| | 1.16 mM T(SH)$_2$; 15 min at 22° C. | 3 mM IAM; 30 min at 220° C. | 57 ± 3 (57)[c] | 0 ± 5 |
| | | 3 mM NEM; 30 min at 220° C. | 251 ± 3 (250)[d] | 24 ± 5 |
| | | 3 mM PAO; 30 min at 220° C. | 154 ± 3 (152)[c] | n.d.[e] |

Tryparedoxin was preincubated in 50 mM Hepes, 1 mM EDTA, pH 7.6 with presumed reducing substrates, then reacted with iodoacetamide (IAM), NEM or phenylarsine oxide (PAO). Changes in molecular mass were determined my MALDI-TOF-MS. Residual activity was measured at 22° C. using 1 mM T(SH)$_2$ with 1.0 µM tryparedoxin peroxidase and 0.6 µM tryparedoxin.
[a]stored under non-reducing conditions
[b]values in brackets represent predicted mass increments
[c]one molecule of derivatising agent
[d]two molecules of derivatising agent
[e]inhibition reversible; activity regained within the timescale of the test The disclosure comprises also that of EP 96 120 015.1, the entire disclosure of which is incorporated herein by reference.

REFERENCES

Bailey, S., Smith, K., Fairlamb, A. H. and Hunter, W. H. (1993) Substrate interactions between trypanothione reductase and N$^1$-glutathionylspermidine disulphide at 0.28-nm resolution. Eur. J. Biochem. 213, 67–75.

Camieri, E. G. S., Moreno, S. N. J. and Docampo, R. (1993) Trypanothione-dependent peroxide metabolism in *Trypanosoma cruzi* different stages. Mol. Biochem. Parasitol. 61, 79–86.

Chance, B., Sies, H. and Boveris, A. (1979) Hydroperoxide metabolism in mammalian organs. Physiol. Rev. 59, 527–605.

Dalziel, K. (1957) Initial steady state velocities in the evaluation of enzyme-coenzyme-substrate reaction mechanisms. Acta Chem. Scand. 11, 1706–1723.

Docampo, R. (1990) Sensitivity of parasites to free radical damage by antiparasitic drugs. Chem. Biol. Interactions 73, 1–27.

Fairlamb, A. H. (1996) Pathways to drug discovery. The Biochemist 18 (February/March), 11–16.

Fairlamb, A. H., Blackburn, P., Ulrich, P., Chait, B. T. and Cerami, A. (1985) Trypanothione: A novel bis (glutathionyl) spermidine cofactor for glutathione reductase in trypanosomatids. Science 227, 1485–1487.

Fairlamb, A. H. and Cerami, A. (1992) Metabolism and functions of trypanothione in the kinetoplastida. Annu. Rev. Microbiol. 46,695–729.

Fairlamb, A. H., Henderson, G. B. and Cerami, A. (1986) The biosynthesis of trypanothione and N1-glutathionylspermidine in *Crithidia fasciculata*. Mol. Biochem. Parasitol. 21, 247–257.

Field, H. and Field, M. C. (1997) Tandem duplication of rab genes followed by sequence divergence and acquisition of distinct functions in *Trypanosoma brucei*. J. Biol. Chem. 272, 10498–10505.

Flohe, L. (1989) The selenoprotein glutathione peroxidase. In: Glutathione—chemical, biochemical, and medical aspects. D. Dolphin, R. Poulson, and O. Avramovic, eds. (New York, USA: J. Wiley and Sons, Inc.) pp. 643–731.

Flohé, L., Loschen, G., Günzler, W. A. and Eichele, E. (1972) Glutathione peroxidase. V. The kinetic mechanism. Hoppe-Seyler's Z. Physiol. Chem. 353, 987–999.

Henderson, G. B., Fairlamb, A. H. and Cerami, A. (1987) Trypanothione dependent peroxide metabolism in *Crithidia fasciculata* and *Trypanosoma brucei*. Mol. Biochem. Parasitol. 24, 39–45.

Jacoby, E. M., Schlichting, I., Lantwin, C. B., Kabsch, W., and Krauth-Siegel, R. L. (1996) Crystal structure of the *Trypanosoma cruzi* trypanothione reductase-mepacrine complex. Proteins 24, 73–80.

LeTrant, N., Meshnick, S. R., Kitchener, K., Eaton, J. W. and Cerami, A. (1983) Iron-containing superoxide dismutase from Crithidia fasciculata. J. Biol. Chem. 258, 125–130.

Nogoceke, E. Gommel, D. U., Kieβ, M., Kalisz, H. M. and Flohé, L. (1997) A unique cascade of oxidoreductases catalyses trypanothione-dependent peroxide metabolism in *Crithidia fasciculata*. Biol. Chem., 378, 827–836.

Penketh, P. G., Kennedy, W. P. K., Patton, C. L. and Sartorelli, A. C. (1987) Trypanosomatid hydrogen peroxidase metabolism. FEBS Lett. 221, 427–431.

Penketh, P. G. and Klein, R. A. (1986) Hydrogen peroxide metabolism in *Trypanosoma brucei*. Mol. Biochem. Parasitol. 20, 111–121.

Risse, H. J. (1993) Afrikanische Trypanosomen—Meister im Austricksens des Immun-systems. In: Extremophile. K. Hausmann, and B.P. Kremer, eds. (Weinheim, Germany: VCH) pp. 361–380.

Shim, H. and Fairlamb, A. H. (1988) Levels of polyamines, glutathione, and glutathione-spermidine conjugates during growth of the insect trypanosomatid *C. fasciculata*. J. Gen. Microbiol. 134, 807–817.

Stone, K. L. and Williams, K. R. (1993) Enzymatic digestion of proteins and HPLC peptide isolation. In: A practical guide to protein and peptide purification for microsequencing, 2nd ed. P. Matsudaira, ed. (London, England: Academic Press Inc.) pp. 45–69.

Tschudi, C., Young A. S., Ruben, L., Patton, C. L. and Richards F. F. (1985) Proc. Nat. Acad.Sci.USA 82, 3998–4002

World Health Organization (1996) Fighting disease, fostering development. World Health Report 1996 (Geneva, Switzerland: WHO).

We claim:

1. A test kit for determining the catalytic activity of a Tryparedoxin (TXN) protein, said protein having an activity which transfers reductive equivalents of trypanothione $(T(SH)_2)$ to a peroxiredoxin, said TXN protein having a molecular weight of between 15 kDA to 19 kDa as determined by mass spectrometry and having a WCPPC motif, wherein the test kit comprises:

a) $(T(SH)_2)$ as a substrate of trypanothione reductase (TR),
   b) isolated TR as a first indicator enzyme;
   c) isolated tryparedoxin peroxidase (TXPNPx), as a second indicator enzyme; and
   d) a hydroperoxide.

2. The test kit of claim 1, wherein the test kit further comprises NADPH as a substrate of TR.

3. The test kit of claim 1, wherein said TXN protein is prepared or isolated from a species of the family Trypanosomatidae.

4. The test kit of claim 1, wherein said kit further comprises a TXN protein.

5. The test kit of claim 1, wherein said test kit is used to determine the catalytic activity of a protein of SEQ ID NO:4.

6. The test kit of claim 1, wherein said TXN protein is prepared or isolated form a species of the Trypanosomatidae family.

7. The test kit of claim 1, wherein said TXN protein catalyzes the reduction of a protein disulfide by trypanothione $(T(SH)_2)$.

8. The test kit of claim 7, wherein said protein disulfide is located in a peroxiredoxin.

9. The test kit of claim 8 wherein said peroxiredoxin is tryparedoxin peroxidase $(TXNP_x)$.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

TCGTGATTCC GTTCCGCATA TGTCAGGGC                                                29

(2) INFORMATION FOR SEQ ID NO: 2:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

GCAACTCAAT CGCTCCCCTC GAGCTTCTTG GCCTCC                                        36

(2) INFORMATION FOR SEQ ID NO: 3:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

CAGCAACTCA ATGGATCCTC ATTACTTCTT GGCC                                          34

(2) INFORMATION FOR SEQ ID NO: 4:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 4:

```
Gly Lys Val Leu Phe Phe Tyr Phe Ser Ala Ser Trp Cys Pro Pro Cys
1               5                   10                  15

Arg Gly Phe Thr Pro Gln Leu Ile Glu Phe Tyr Asp Lys Phe His Glu
                20                  25                  30

Ser Lys Asn Phe Glu Val Val Phe Cys Ser Trp Asp Glu Glu Glu Asp
            35                  40                  45

Gly Phe Arg Gly Tyr Phe Ala Lys Met Pro Trp Leu Ala Val Pro Phe
        50                  55                  60

Ala Gln Ser Glu Ala Val Gln Lys Leu Ser Lys His Phe Asn Val Glu
65                  70                  75                  80
```

(2) INFORMATION FOR SEQ ID NO: 5:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

```
GGSAARCTRG TSTTCTTCTA CTTCTCCGCG AGCTGGTGCC CGCCGTGCGC GGGCTTCACG      60

CCGCAGCTGA TCGAGTTCTA CGACAAGTTC CACGAGTCGA AGAACTTCGA GGTTGTGTTC     120

TGCACGTGGG ACGAGGAGGA GGACGGCTTT GCGGGCTACT TCGCGAAGAT GCCGTGGCTT     180

GCGGTGCCGT TTGCGCAGAG CGAGGCGGTG CAGAAGCTGT CGAASCASTT CAACGTCGAG     240
```

(2) INFORMATION FOR SEQ ID NO: 6:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 6:

```
Met Ser Gly Leu Lys Lys Phe Phe Pro Tyr Ser Thr Asn Val Leu Lys
1               5                   10                  15

Gly Asp Ala Ala Asp Ile Ala Leu Pro Ser Leu Ala Gly Lys Thr Val
                20                  25                  30

Phe Phe Tyr Phe Ser Ala Ser Trp Cys Pro Pro Cys Arg Ala Phe Thr
            35                  40                  45

Pro Gln Leu Ile Glu Phe Tyr Lys Ala His Ala Glu Lys Lys Asn Phe
        50                  55                  60

Glu Val Met Leu Ile Phe Trp Asp Glu Ser Ala Glu Asp Phe Lys Asp
65                  70                  75                  80

Tyr Tyr Ala Lys Met Pro Trp Leu Ala Leu Pro Phe Glu Asp Arg Lys
                85                  90                  95

Gly Met Glu Phe Leu Thr Thr Gly Phe Asp Val Lys Ser Ile Pro Thr
                100                 105                 110
```

Leu Val Gly Val Glu Ala Asp Ser Gly Asn Ile Ile Thr Thr Gln Ala
        115                 120                 125

Arg Thr Met Val Val Lys Asp Pro Glu Ala Lys Asp Phe Pro Trp Pro
    130                 135                 140

Asn Val Glu Ala Lys Lys
145                 150

(2) INFORMATION FOR SEQ ID NO: 7:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

| | | |
|---|---|---|
| ATGTCAGGGC TGAAGAAGTT CTTCCCTTAC AGCACAAACG TGCTGAAGGG TGCTGCTGCG | 60 |
| GATATCGCGC TCCCCTCGCT GGCGGGCAAG ACCGTATTCT TCTACTTCTC CGCGAGCTGG | 120 |
| TGCCCGCCGT GCCGGGCCTT CACGCCGCAG CTGATCGATT TTTACAAGGC CCACGCGGAG | 180 |
| AAGAAGAACT TCGAGGTGAT GCTCATCTCC TGGGATGAGT CAGCAGAGGA CTTTAAGGAC | 240 |
| TACTACGCGA AGATGCCGTG GCTGGCATTG CCGTTTGAAG ACCGCAAAGG GATGGAGTTC | 300 |
| TTGACGACCG GCTTCGATGT GAAGTCGATC CCAACCTTGG TGGGCGTCGA GGCGGACTCG | 360 |
| GGAAACATCA TCACAACGCA GGCGCGTACG ATGGTGGTGA AGGACCCGGA AGCAAAGGAT | 420 |
| TTTCCGTGGC CCAACGTGGA GGCCAAGAAG TAA | 453 |

(2) INFORMATION FOR SEQ ID NO: 8:

(i) SEQUENCE CHARACTERISTICS:
        (A) LENGTH: 727 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 8:

| | | |
|---|---|---|
| GAAGTATCTT GTAGTGGTAC ACTTCTCACA TACAACACAA CTTATTCTTT GCTTTTTCAC | 60 |
| TTTGTCTGTG TGTTGAAGCA CTCGCACATC ACGCCTCGTT GCCGCACCGC GCACAAGGCT | 120 |
| CTACGGTTTC GCTCACGCTG AGTCGGGGTG CATGTATCAC ACCCTTCTCT ACGACTTTCG | 180 |
| TGATTCCGTT CCGCACATGT CAGGGCTGAA GAAGTTCTTC CCTTACAGCA CAAACGTGCT | 240 |
| GAAGGGTGCT GCTGCGGATA TCGCGCTCCC CTCGCTGGCG GGCAAGACCG TATTCTTCTA | 300 |
| CTTCTCCGCG AGCTGGTGCC CGCCGTGCCG GGCCTTCACG CCGCAGCTGA TCGATTTTTA | 360 |
| CAAGGCCCAC GCGGAGAAGA AGAACTTCGA GGTGATGCTC ATCTCCTGGG ATGAGTCAGC | 420 |
| AGAGGACTTT AAGGACTACT ACGCGAAGAT GCCGTGGCTG GCATTGCCGT TTGAAGACCG | 480 |
| CAAAGGGATG GAGTTCTTGA CGACCGGCTT CGATGTGAAG TCGATCCCAA CCTTGGTGGG | 540 |
| CGTCGAGGCG GACTCGGGAA ACATCATCAC AACGCAGGCG CGTACGATGG TGGTGAAGGA | 600 |

```
CCCGGAAGCA AAGGATTTTC CGTGGCCCAA CGTGGAGGCC AAGAAGTAAA GGGGAGCGAT        660

TGAGTTGCTG CAGGCGTGCG TGAAGCACCT TTATATTTTT CCTTTTTCTT CTCCTGTAGG        720

CTGCGTG                                                                  727
```

(2) INFORMATION FOR SEQ ID NO: 9:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 9:

```
Met Ser Leu Leu Ala Gly Val Lys Leu Glu Lys Arg Asp Lys Thr Leu
1               5                   10                  15

Val Asp Ala Thr Glu Ala Leu Ala Gly Lys Ala Val Gly Phe Tyr Phe
            20                  25                  30

Ser Ala His Trp Cys Pro Pro Cys Arg Gly Phe Thr Pro Ile Leu Lys
        35                  40                  45

Asp Phe Tyr Glu Glu Val Glu Asp Glu Phe Glu Val Val Phe Val Ser
    50                  55                  60

Phe Asp Arg Ser Glu Ser Asp Leu Lys Met Tyr Met Ser Glu His Gly
65                  70                  75                  80

Asp Trp Tyr His Ile Pro Tyr Gly Asn Asp Ala Ile Lys Glu Leu Ser
                85                  90                  95

Thr Lys Tyr Gly Val Ser Gly Ile Pro Ala Leu Ile Ile Val Lys Pro
            100                 105                 110

Asp Gly Thr Glu Val Thr Lys Asp Gly Arg Asn Asp Val Gln Asn Gly
        115                 120                 125

Lys Asp Pro Lys Ala Thr Val Ala Lys Trp Lys Ala
    130                 135                 140
```

(2) INFORMATION FOR SEQ ID NO: 10:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 10:

```
Ser Leu Ala Gly Lys Leu Val Phe Phe Tyr Phe Ser Ala Ser Trp Cys
1               5                   10                  15

Pro Pro Cys Arg Gly Phe Thr Pro Gln Leu Ile Glu Phe Tyr Asp Lys
            20                  25                  30

Phe His Glu Ser Lys
        35
```

(2) INFORMATION FOR SEQ ID NO: 11:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 11:

Met Pro Trp Leu Ala Val Pro Phe Ala Gln Ser Trp Ala Val Gln Lys
1               5                  10                  15

(2) INFORMATION FOR SEQ ID NO: 12:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 12:

His Phe Asn Val Glu Ser Ile Pro Thr Leu Ile Gly Val Asp Ala Asp
1               5                  10                  15

Ser Gly Asp Val Val Thr Thr Arg
            20

(2) INFORMATION FOR SEQ ID NO: 13:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 13:

Ala Thr Leu Val Lys Asp Pro Glu Gly Glu Gln Phe Pro Ser Lys Asp
1               5                  10                  15

Ala (2) INFORMATION FOR SEQ ID NO: 14:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 14:

```
Phe Tyr Asp Lys Phe His Glu
1               5

(2) INFORMATION FOR SEQ ID NO: 15:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: misc.
        (B) LOCATION: 23
        (D) OTHER INFORMATION: /note= "Xaa=Unknown or Other"

(xi) SEQUENCE DESCRIPTION: SEQ ID NO: 15:

Ser Ile Pro Thr Leu Ile Gly Val Asp Ala Asp Ser Gly Asp Val Val
1               5                   10                  15

Thr Thr Arg Ala Arg Ala Xaa Leu Val Lys
            20                  25
```